United States Patent [19]
Sherratt et al.

[11] Patent Number: 5,972,708
[45] Date of Patent: Oct. 26, 1999

[54] PLASMID STABILIZATION

[75] Inventors: David J. Sherratt, Witney; Steven G. Williams; Julian A.J. Hanak, both of Cheshire, all of United Kingdom

[73] Assignee: Cobra Therapeutics Limited, Keele, United Kingdom

[21] Appl. No.: 09/176,607

[22] Filed: Oct. 21, 1998

Related U.S. Application Data

[63] Continuation of application No. 08/708,921, Sep. 6, 1996, abandoned
[60] Provisional application No. 60/004,271, Sep. 25, 1995.

[30] Foreign Application Priority Data

Sep. 8, 1995 [GB] United Kingdom ............... 9518395

[51] Int. Cl.$^6$ ............... C12N 1/68; C12N 1/21; C12N 15/85; C12N 15/63
[52] U.S. Cl. ............... 435/479; 435/6; 435/69.1; 435/252.3; 435/252.33; 435/254.2; 435/320.1; 435/325; 435/440; 435/455; 435/463; 435/466; 435/476; 435/483; 536/23.1
[58] Field of Search ............... 435/6, 69.1, 320.1, 435/252.3, 252.33, 325; 536/23.1; 514/44

[56] References Cited

U.S. PATENT DOCUMENTS

| | | | |
|---|---|---|---|
| 4,920,048 | 4/1990 | Diderichsen | 435/69.1 |
| 5,015,573 | 5/1991 | Yarranton et al. | 435/69.1 |
| 5,763,270 | 6/1998 | Eastman et al. | 435/320.1 |

FOREIGN PATENT DOCUMENTS

| | | |
|---|---|---|
| 0 106 542 | 4/1984 | WIPO . |
| WO 94/02609 | 2/1994 | WIPO . |

OTHER PUBLICATIONS

Gossen, et al., "Control of gene activity in higher eukaryotic cells by prokaryotic regulatory elements", *TIBS*, 1993, 18, 471–475.

Lebedeva, et al., "A new T7 RNA polymerase–driven expression system induced via thermoamplification of a recombinant plasmid carrying a T7 promoter—*Escherichia coli* lac operator", *Gene*, 1994, 142, 61–66.

*Primary Examiner*—John L. LeGuyader
*Attorney, Agent, or Firm*—Woodcock Washburn Kurtz Mackiewicz & Norris LLP

[57] ABSTRACT

A system is described which utilizes a novel system of repressor titration for maintenance of a plasmid useful in gene therapy and production of a recombinant protein. The system utilizes a transformed host cell containing a plasmid including an operator susceptible to binding by a repressor expressed in trans, a first chromosomal gene encoding the repressor, and a second chromosomal gene that is functionally associated with an operator and essential for cell growth, wherein the plasmid is present in the cell in sufficient numbers to titrate the repressor such that the essential gene is expressed, thereby permitting cell growth.

18 Claims, 7 Drawing Sheets

PLASMID STABILIZATION

This Application is a continuation of application Ser. No. 08/708,921 filed Sep. 6, 1996, now abandoned, which claims priority from provisional application Ser. No. 60/004,271 filed Sep. 25, 1995 incorporated by reference in their entireties.

FIELD OF THE INVENTION

This invention relates in general to stable maintenance of a plasmid, and in particular to a plasmid containing a gene useful in gene therapy.

BACKGROUND OF THE INVENTION

The stable maintenance of a plasmid, particularly at high copy number, is important for the preparation of DNA carrying a therapeutic gene for use in gene therapy. However, extrachromosomal DNA carried in host cells is inherently unstable in cell culture because cultured cells which contain plasmids usually have an increased metabolic burden compared to plasmid-free segregant cells. In efforts to maintain plasmid stability and decrease metabolic burden, plasmids engineered to contain dominant selectable markers have been routinely used. During scale-up fermentation of bacterial or yeast host strains, the presence of the selecting agent prevents plasmid loss and overgrowth by cells not burdened by the effort of replication and maintenance of plasnid DNA.

Antibiotic resistance genes, for example encoding resistance to antibiotics such as ampicillin, kanamycin or tetracycline, are the most common dominant selectable markers used in molecular biology cloning and fermentation procedures for the production of recombinant proteins or plasmid DNA. For continuous fermentation in the presence of an antibiotic, selective pressure is lost because the antibiotic loses activity over time due to culture dilution or degradation by the host cell. Therefore, some of the more successful methods for maintaining plasmids do not utilize antibiotic selection but rather rely on a mutant host which is unable to synthesize an amino acid and inserting the gene which provides for this synthesis in the plasmid. Other solutions which prevent the takeover of a culture by plasmid-free segregant involve placing a gene coding for a toxic product in the chromosome and then including a corresponding repressor system in the plasmid. Plasmid-free cells are effectively killed upon segregation. Even with selective pressure, however, plasmid-free cells may continue to grow due to leakage of the complementing product of the selective gene from plasmid-bearing cells. In addition, the use of genes for antibiotic resistance or other dominant selectable markers on vectors intended for gene therapy has raised potential problems related to expression of those genes in the target mammalian cell or host mammalian organism. Expression of the those genes in the target mammalian cell may lead to its destruction and/or to an antigenic response to the gene product in the mammal. There are also concerns regarding contamination of the final product with the antibiotic used for plasmid selection in culture, with the potential induction of a severe immune response to the antibiotic, e.g., anaphylactic shock. The wide-spread use of bacterial genes for antibiotic resistance also will ultimately result in their transfer to the bacterial population as a whole. There is, therefore, a need for a method of plasmid maintenance that does not require the presence of plasmid borne genes or antibiotic selection.

SUMMARY OF THE INVENTION

The invention is based on the discovery of a plasmid maintenance system which does not require the use of a plasmid-borne dominant selectable marker, but rather utilizes a system of repressor titration.

The invention encompasses a transformed host cell containing a plasmid comprising an operator susceptible to binding by a repressor expressed in trans, a first chromosomal gene encoding the repressor, and a second chromosomal gene that is functionally associated with an operator and essential for cell growth, wherein the plasmid is present in the cell in sufficient numbers to titrate the repressor such that the essential gene is expressed, thereby permitting cell growth.

As used herein, "functionally associated" or "operatively associated", with respect to an operator sequence and an associated gene, means that the operator is linked in cis to the gene such that expression of the gene is susceptible to repression upon binding of a repressor to the operator. It will be understood by one of skill in the art that the operator sequence present on the plasmid need not be a sequence that is identical to the operator sequence on the chromosomal gene, in that the plasmid operator need only consist of the minimal sequences necessary for binding the repressor that represses transcription of the chromosomal gene. It will also be understood that mutated operator sequences are also useful according to the invention, for example, sequences having one or more nucleotides inserted, deleted, or substituted which result in increased or decreased affinity for the corresponding repressor.

As used herein, "cell growth" refers to increasing numbers of cells in a culture medium over time, and also refers to cell survival where the number of cells does not increase over time, but rather the number of live cells does not decrease over time.

Preferably, the repressor gene encodes one of the E. coli lac repressor, the λ repressor, the E.coli trp repressor, E.coli the galR repressor, the E. coli araC repressor, the E. coli ArgRNV repressor (Burke et al. (1994) Mol. Microbiol., 13, 609–618) and the E. coli Tet repressor. As described above, each repressor is operative in trans with a trans-associated operator sequence that is present both in the chromosome and on the plasmid. The invention contemplates the presence of one or more repressor genes on the host chromosome, e.g., one, two or three repressor genes, in order to ensure plasmid stability where one chromosomal repressor gene becomes mutated or deleted.

Preferred operator sequences therefore include the lac operator, the λ operator, the trp operator, the gal operator, the ara operator, the Arg operator and the Tet operator. If desired, the corresponding promoter may be functionally associated with its operator.

The host cell may be any cell including animal cells such as mammalian cells and insect cells, plant cells, fungi such as yeast and bacteria.

In a preferred embodiment, the host cell is a bacterial cell that may be either gram negative or positive, for example, E. coli, Salmonella, Bacillus, Streptomyces and Lactobacillus.

When the host cell is a eukaryotic cell, the Lac and Tet repressors and their corresponding operators are preferably used.

More than one different essential chromosomal gene that is functionally associated with the operator may be present in the cell chromosome, wherein the essential gene is linked to an operator and therefore susceptible to repression by the repressor, to guard against loss of repressor susceptibility at one chromosomal operator. In one preferred embodiment of the invention, the gene encoding the repressor protein is present in two or three copies at different locations in the chromosome to guard against loss of repressor expression at one chromosomal location.

Preferred essential genes that are located on the host chromosome include but are not limited to genes falling within the following categories: genes encoding products related to the biosynthesis of cell metabolites such as cell wall precursors, genes whose products are involved in carbon metabolism, genes coding for antibiotic resistance, and genes encoding biosynthesis or regulation of macromolecules, e.g., genes essential for DNA and/or RNA synthesis and replication functions.

Preferably, the plasmid comprises an origin of replication permitting replication of about 10–200 copies of the plasmid per host cell, for example 10–20 copies or as much as about 100–200 copies of the plasmid per host cell.

It is preferred that the plasmid includes a cloning site for insertion of a gene of interest.

In one especially preferred embodiment of the invention, the plasmid further includes a gene of interest. Preferably, the gene of interest is expressible in a mammalian, preferably a human, cell. Examples of such genes are known in the art and disclosed herein. If desired, the gene of interest will not be expressed in the host strain. Where the host strain is a bacterium, this can be achieved by not including a bacterial promoter operatively associated with the gene of interest. In addition, if desired, the gene of interest may be associated with the plasmid operator sequence such that expression of this gene is repressible upon growth of the plasmid-transformed host cell. These serve to reduce the metabolic burden to the host cell of producing the encoded protein of interest. Alternatively, if expression of the gene of interest is desired, e.g., where it is desirable to produce and isolate the encoded product, the operator need not be positioned so as to repress expression of the gene of interest upon cell growth and expression of the gene of interest may be driven by a promoter active in the host cell.

The invention also encompasses the above-described host cell wherein the plasmid includes only those sequences necessary for its replication and maintenance in the host cell. That is, wherein the plasmid consists essentially of an operator susceptible to binding by a repressor expressed in trans, an origin of replication, and a cloning site for insertion of a gene of interest.

The invention also encompasses the above-described minimal plasmid, i.e., consisting essentially of an operator susceptible to binding by a repressor expressed in trans, an origin of replication, and a cloning site for insertion of a gene of interest. As used herein, "consisting essentially of" refers to the plasmid sequences and means that the plasmid contains only those sequences necessary for maintaining the plasmid in the host strain, and a cloning site for insertion of a therapeutic gene. That is, the plasmid does not contain additional plasmid sequences that are unnecessary to its survival in the host cell, although it may contain additional non-plasmid sequences, e.g., an expressible mammalian gene. As used herein, "origin of replication" refers to those sequences on the plasmid that are necessary for maintaining the plasmid at a given copy number per cell.

Preferably, this minimal plasmid is about 1000 bp in length. More preferably, the minimal plasmid is about 2 Kb in length, wherein DNA contained in the plasmid that is other than the operator sequence, the origin of replication, and the cloning site is non-coding DNA.

It is especially preferred that this minimal plasmid further contain a gene of interest operatively associated with control sequences for expression in the target cell. Preferably the target cell is a mammalian cell and more preferably a human cell.

The minimal plasmid possesses the considerable advantage of containing only minimal foreign DNA sequences such as bacterial sequences, and thus considerably reduces the problems associated with the introduction of foreign DNA sequences into mammalian cell lines, for example, where a plasmid is intended as a vector for gene therapy. Thus, problems that are avoided according to the invention include expression of plasmid-borne genes such as bacterial or yeast genes in a mammalian target cell which lead to destruction of the target cell or the mammalian host itself, or which lead to development of an immune response to the foreign DNA or to products encoded by such sequences.

The invention also encompasses a method of maintaining a plasmid in a host cell, comprising the step of culturing the above-described transformed cell for a time and under conditions sufficient to permit the cell to grow.

The invention also encompasses a method of producing plasmid DNA, comprising culturing the above-described transformed cell for a time and under conditions sufficient to permit the cell to grow, and isolating plasmid DNA from the cultured cell.

The invention also encompasses a method of producing a recombinant protein, comprising culturing the above-described transformed host cell for a time and under conditions sufficient to produce the recombinant protein. Preferably, the method further comprising isolating the recombinant protein. Preferably, the recombinant protein is a protein of therapeutic benefit to a human.

Production of a recombinant protein using the repressor titration system described herein confers a reduced metabolic burden on the host cell in that the only coding region on the plasmid is the gene encoding the recombinant protein. Therefore, the host cell need not support production of plasmid-encoded proteins other than the recombinant protein. In addition, the repressor titration system described herein allows for production of a recombinant protein in the absence of an antibiotic, thus avoiding loss of plasmid selection due to loss of antibiotic activity in the culture. Furthermore, the isolated recombinant protein will not be contaminated with an antibiotic.

The repressor titration system described herein enables the stable maintenance of plasmids in moderate or high copy number without the use of plasmid-encoded dominant selectable markers, such as for antibiotic resistance, and can be used with any host that can support a trans-acting repressor/operator system. One advantage of the invention is in its reliance on plasmid maintenance other than by antibiotic selection of plasmid-bearing cells. That is, there is no loss of selective pressure during fermnentation due to loss of activity of an antibiotic. The absence of dominant selectable markers, such as antibiotic resistance genes, on the plasmid, as described herein, is also advantageous in that it avoids the potentially serious problems related to expression of those genes in a target mammalian cell. The invention thus also avoids contamination of a product intended for gene therapy with the antibiotic used for selection of the gene therapy vector. In addition, the invention avoids the potential induction of a severe immune response to such antibiotics, e.g., anaphylactic shock.

One considerable advantage to the plasmid stabilization system described herein is that it avoids wide-spread use of bacterial genes encoding antibiotic resistance, which use tends to promote transfer of such genes in the bacterial population as a whole.

Other features and advantages of the invention will be apparent from the following description of the preferred embodiment thereof and from the claims.

BRIEF DESCRIPTION OF THE DRAWINGS

Before describing the invention in detail, the drawings will be described.

DESCRIPTION

The invention is illustrated by the following nonlimiting examples wherein the following materials and methods are employed. The entire disclosure of each of the literature references cited hereinafter are incorporated by reference herein.

Figure 1:
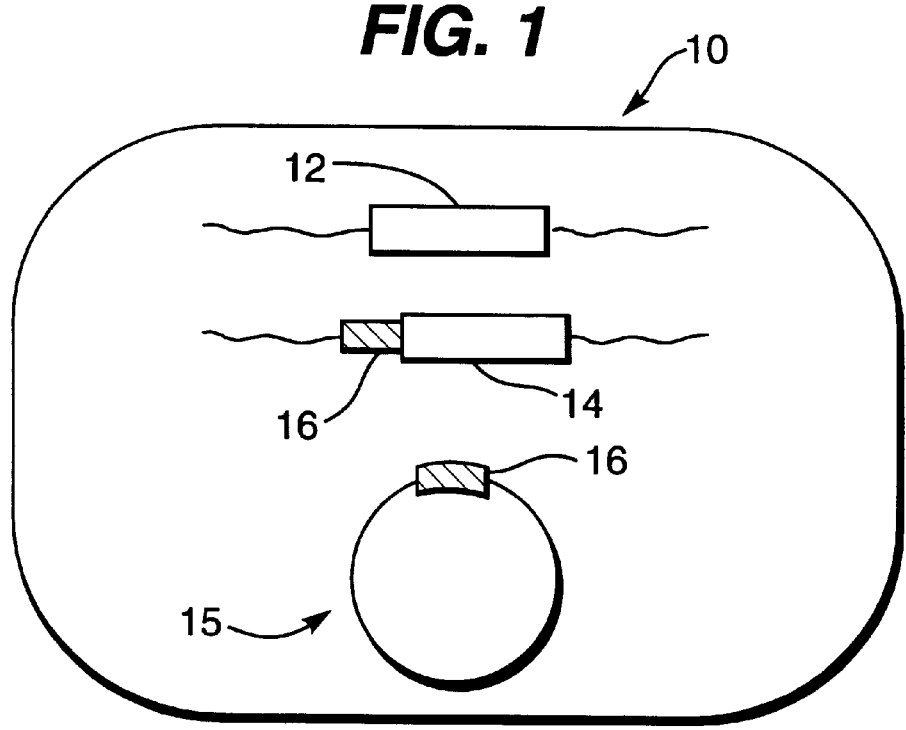
FIG. 1 is a schematic drawing of a plasmid-transformed host cell according to the invention.
Figure 2:
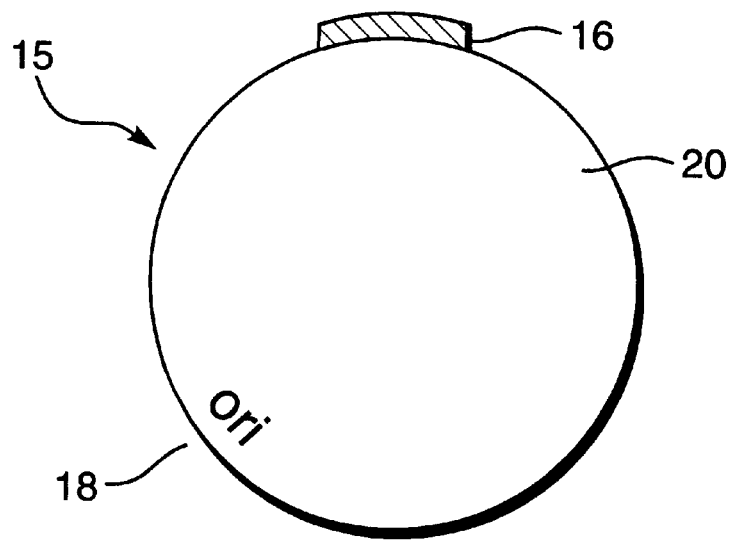
FIG. 2 is a schematic drawing of a minimal plasmid according to the invention.
Figure 3A:
FIG. 3 is an agar plate containing minimal medium with lactose or glucose as the sole carbon source, and shows growth of E. coli strain Hfr 3000 YA694 untransformed and transformed with pUC18, A) Hfr 3000 YA694 (min/glu/B1), B) Hfr 3000 YA694 (min/lac/B1), C) Hfr 3000 YA694-pUC18 (min/glu/B1/Ap), D) Hfr 3000 YA694-pUC18 (min/lac/B1/Ap)
Figure 3B:
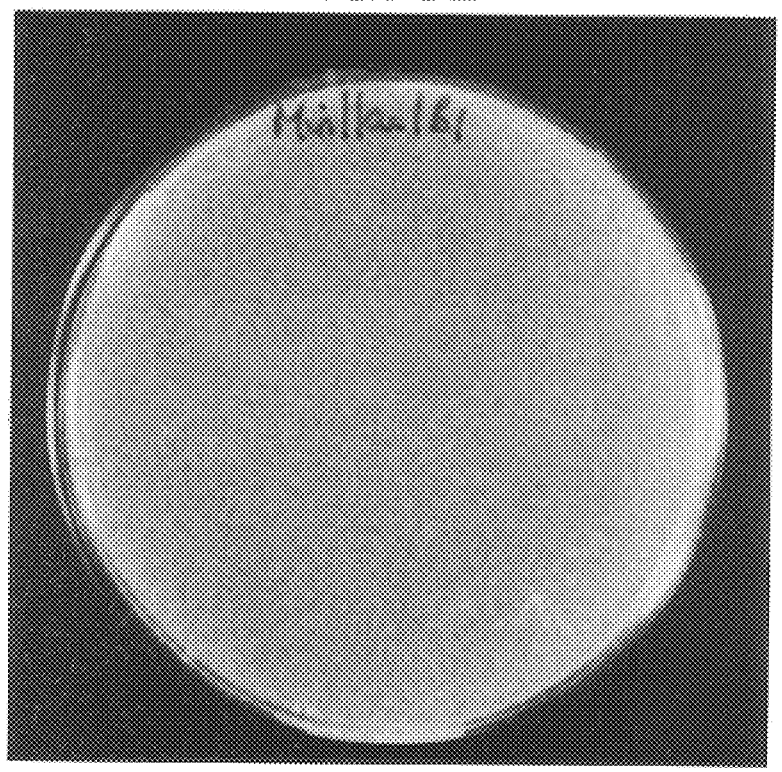
Figure 3C:
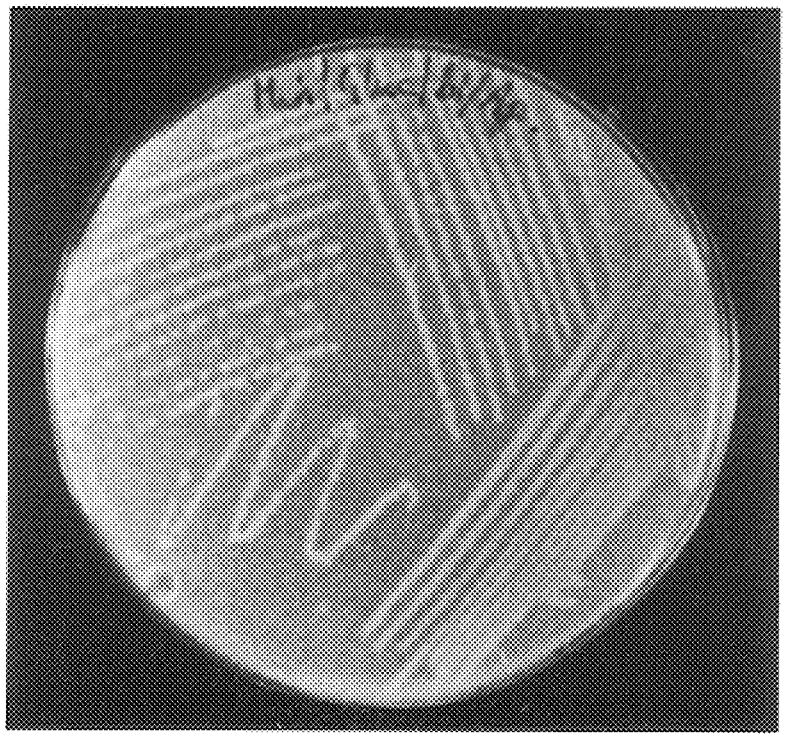
Figure 3D:

The invention is based on transformed host cells, plasmids, and methods for improved production and maintenance of a plasmid in a host cell using a novel system of repressor titration (FIG. 1). Plasmid DNA produced according to the invention is useful in gene therapy. The plasmid itself may consist of certain minimal sequences, as shown in FIG. 2, and is capable of carrying a therapeutic gene of interest. The novel repressor titration system works as follows.

The system, as presented in FIGS. 1 and 2, utilizes a host cell 10 transformed with a plasmid-borne repressor protein binding sequence 16, i.e., an operator, and a host chromosomal copy of a gene encoding a repressor protein 12. Another chromosomal gene 14, the product of which is essential for growth or survival of the host cell, is operatively associated with (i.e., placed under the control of) an operator 16 that binds the repressor protein. In the absence of plasmid 15, binding of repressor to the chromosomal operator prevents expression of the essential gene, and the cell can only grow in the presence of inducer. Subsequent introduction of a plasmid that contains a binding site for the repressor protein results in the titration of the repressor protein away from the chromosomal operator, thus allowing expression of the essential gene. Therefore, in the absence of inducer, only those cells that contain the plasmid will grow. This is because the presence of the operator sequence on the plasmid allows the plasmid to titrate the repressor, thus removing repressor molecules which would otherwise be available for binding to the chromosomal operator. Titration of repressor by plasmid operator sequences allows for expression of the essential chromosomal gene, and growth of only those cells containing plasmid. If the host strain is engineered so that repressor is synthesized at a high copy number, then the plasmid will be maintained at an even higher copy number.

As shown in FIG. 2, the plasmid 15 need only include sequences for operator binding 16, and origin of replication 18, and a cloning site 20.

Repressor/Operator Systems Useful According to the Invention.

The invention can be used with any trans-acting repressor/operator system. For example, the repressor titration system described herein may include any repressor that has a sufficient affinity for its DNA binding sequence such that it is capable of preventing expression of an essential chromosomal gene, but is also titratable by a plasmid-bome DNA binding sequence.

The essential chromosomal gene which is susceptible to repression by the repressor is rendered susceptible to repression in that it is placed under the control of an operator/promoter that binds the repressor, or the repressor binding sequence (i.e., operator) is inserted into or associated with the natural promoter of the essential gene in such a way that it can prevent transcription when bound by repressor, but does not disrupt the ability of the natural promoter to initiate transcription of the essential gene in the absence of repressor binding.

More than one different essential gene may be present in the chromosome, e.g., two or three genes, each gene being functionally linked to an operator sequence and thus susceptible to repression by the repressor. The presence of different repressor-susceptible essential genes on the chromosome, preferably at different positions in the chromosome, reduces the possibility of loss of plasmid stability via a mutation or deletion resulting in loss of repression of an essential chromosomal gene.

The repressor is encoded by a chromosomal gene. According to the invention, one or more, preferably one, two, or three, copies of the chromosomal repressor gene are present in the host cell. The chromosomal repressor gene may be a naturally occurring gene which has not been modified, or it may contain a genetic mutation that renders the repressor molecule of higher or lower affinity with respect to the strength of binding to its corresponding operator. Such mutations are known in the prior art, for example, the affinity of the lac repressor for its operator can be enhanced by single amino acid changes (see Betz, (1986) Gene, 42, 283–292 and Khoury et al., (1991) J. Mol. Biol., 219, 623–634). Alternatively, more or less copies of the operator binding site can be introduced into the plasmid or more or less copies of the repressor gene can be introduced onto the chromosome or in an alternative embodiment carried on a plasmid.

Alternatively, the sequences which initiate expression of the repressor gene such as promoters, enhancers etc. may be mutated or genetically engineered such that a higher or lower number of repressor molecules are made in the cell. For example, the number of copies of the lac/d repressor can be increased by the introduction of the lacIq mutation (see Carlos (1978) Nature 274, 762–765). The number of repressor molecules present in the cell will be related to the copy number of the plasmid bearing the corresponding operator sequence. According to the repressor titration system of the invention, the concentration of repressor present in the host cell is such that, in the absence of the plasmid, the essential gene of interest is not expressed, but in the presence of the plasmid, repressor is titrated away from the essential gene. Where more than one copy of the repressor gene is present in the chromosome, e.g., two or three copies, the amount of repressor protein made in the cell will be increased relative to the presence of one gene, this increase will be taken into account when selecting a corresponding plasmid origin of replication, and in selecting the number of chromosomal operator/essential genes which are present in the cell.

The strength of the operators and the affinities of the repressors may be altered to tailor the system for use with plasmids of different copy number. For example, the extent of repression of the lac operon can be enhanced by the introduction of an optimally placed auxiliary ideal lac operator (i.e. a lac operator having enhanced repressor affinity), or the introduction of the ideal operator within the promoter (Muller et al., (1996) Mol. Biol., 257, 21–29 and Lewis et al., (1996) Science 271, 1247–1254). Alternatively, the strength of the operator could be reduced by the introduction of a non-ideal operator, non-optimal positioning of the operator or elimination of an auxiliary operator (Muller et al., (1996) Mol. Biol., 257, 21–29 and Oehler et al., (1990) EMBO J. 219,973–979). For example, the affinity of the lac repressor for its operator can be enhanced by single amino acid changes (Betz, (1986) Gene, 42, 283–292).

Repressor systems useful according to the invention include but are not limited to the following. The *E. Coli* lac repressor is described in "The Lactose Operon", J. Beckwith, in Escherichia coli and Salmonella typhimurium, Eds., J. L. Ingraham et al., 1987 Amer. Soc. Micro., pp. 1444–1452, and Dickson et al., 1975, Science 187:27–35. The lac operon is regulated as follows. Under non-inducing conditions (such as growth on glucose) LacI binds to the operator of the lac operon and prevents transcription of β galactosidase (LacZ), lactose permease (LacY) and a transacetylase (LacA). Under inducing conditions (such as growth on lactose or addition of IPTG, a non-metabolizable analog) the repressor no longer binds to the operator and transcription occurs. The expression of the operon is easily detected by assay for β-galactosidase. Other repressor systems useful according to the present invention include the lac repressor system described above and the tet repressor system for use in regulating gene activity in eukaryotic cells (Gossen et al., (1994) Current Opinions in Biotechnology, 5, 516–520). The tet repressor system has been used in yeast, dictiostelium, plant cells and tobacco plants. A further repressor system useful according to the present invention is the ArgRNV repressor system (Burke et al., (1994) Mol. Microbiol. 13, 609–618). The ArgR repressor normally only binds to its operator in the presence of Arginine. However, the mutant ArgRNV repressor binds to the operator in the absence of arginine and remains bound in the presence of arginine and has a transdominant effect. An idealised ArgR binding site (operator) having two symmetrical Arg boxes, can be engineered into the plasmid of interest to enable the titration of ArgRNV away from an essential gene the expression of which is controlled by the ArgR binding site.

One of skill in the art will appreciate that certain modifications may be made to the repressor-titration system described herein which serve to adapt the system to a given protocol. For example, where the growth medium contains components which induce rather than allow for repression of the operator, and inducing conditions are not desired during growth, operator or repressor mutants may be used to overcome induction and allow for repression. One example of a mutant repressor is a LacI mutant of the lac repressor. A LacI mutant no longer has the capacity to bind inducer. Examples of LacI mutants include, e.g., LacI$^s$ mutants (Beyreuthe, 1978, Cold Spring Harbor Laboratory, CSH, NY) and other mutants such as Asp276—>Asn274 (Chang et al., 1994, Biochem. 22:3607–3616). By replacing the wild type repressor with a mutant repressor which is insensitive to inducer, the repressor is able to bind to the operator during growth, and the plasmid is maintained in the host cell even under conditions which normally induce the repressor.

The *E. coli* trp repressor also is useful according to the invention (see "The tryptophan Operon", Yanofsky and Crawford, in Escherichia coli and Salmonella typhimurium, Eds., J. L. Ingraham et al., 1987, Amer. Soc. Micro., pp. 1453–1472). The trp repressor is present at about 50 copies/cell, and requires the presence of tryptophan in the fermentation medium as an inducer of repressor binding. The *E. coli* galR repressor also is useful according to the invention (see "The Galactose Operon", S. Adhya, in Escherichia coli and Salmonella typhimurium, Eds., J. L. Ingraham et al., 1987, Amer. Soc. Micro., pp. 1503–1512). The *E. coli* araC repressor is also useful according to the invention (see "The L-Arabinose Operon", R. Schlief, In Escherichia coli and Salmonella typhimurium, Eds., J. L. Ingraham et al., 1987, Amer. Soc. Micro., pp. 1473–1481, Dunn et al., 1984, Proc. Nat. Aca. Sci. 81;5017–5020). The araC repressor has increased binding affinity in the presence of arabinose. Finally, the λ repressor is useful according to the invention (Introduction to Lambda Phages, in Current Protocols in Molecular Biology, Eds. Ausubel, et al., 1994, Section III, Unit 1.9; Hochschild et al., 1986, Cell 47(5);807–816).

Plasmids Useful According to the Invention.

The invention can be utilized advantageously with a plasmid origin of replication that permits replication of at least 10, preferably at least 20–100, and most preferably at least 200–500 copies of the plasmid per host cell. Those origins of replication that permit replication of moderate (i.e., 20–50) to high plasmid (i.e., 200–500) copy numbers are especially useful in that moderate to high plasmid copy numbers can easily titrate repressor molecules. Of course, if desired, a plasmid having a copy number as high as 1000–2000 copies per cell also may be used.

Plasmids with low copy numbers (i.e., 10 copies—1 copy/cell) are most advantageously used according to the invention after mutation to bring about increased copy number (J. Scott, 1984, Microbial Reviews 48:1–23). Of the frequently used origins of replication, pBR322 (about 20 copies/cell) is useful according to the invention, and pUC (at about 200 copies/cell) is preferred. Examples of such plasmids include but are not limited to pBR322 and the pUC series of plasmids as described by Vieira & Messing (1982, Gene, 19(3), 259–268 and Yanisch-Perron et al. (1985, Gene, 33(1), 103–119), herein referred to as pUC. Although not preferred, other plasmids which are useful according to the invention are those which require the presence of plasmid encoded proteins for replication, for example, the pT181, FII, and FI origins of replication.

Examples of origins of replication which are useful according to the invention in *E. coli* and *S. typhimurium* include but are not limited to pMB1 (25 or more copies per cell, Bolivar et al., 1977, Gene 2:95–113), CoEI (15 or more copies per cell, Kahn et al., 1979, Methods Enzymol. 68:268–280), p15A (about 15 copies per cell, Chang et al., 1978, J. Bacteriol. 134:1141–115 6); pSC101 (about 6 copies per cell, Stoker et al., 1982, Gene 18:335–341); R6K (less than 15 copies per cell, Kahn et al, 1979, supra); R1 (temperature dependent origin of replication, Uhlin et al, 1983, Gene 22:255–265); lambda dv (Jackson et al., 1972, Proc. Nat. Aca. Sci. 69:2904–2909). An example of an origin of replication that is useful in Staphylococcus is pT181

(about 20 copies per cell, J. Scott, 1984, Microbial Reviews 48:1–23. Of the above-described origins of replication, pMB1, p15A and ColE1 are preferred because these origins do not require plasmid-encoded proteins for replication.

Plasmid origins of replication useful according to the invention, including origins or replication from vectors for *E. coli*, vectors for gram-negative bacteria, vectors for streptomyces, vectors for gram-positive bacteria such as Bacillus, Staphylococcus and Streptococcus, vectors for fungi, yeasts containing for example 2 micron or ARS replicons, and plant cells, vectors for animal cells, for example containing SV40 and BPV replicons, vectors for Cyanobacteria, Haemophilus, and Neisseria, are described in detail in Cloning Vectors, A Laboratory Manual, Pouwels et al., eds., 1985, Elsevier, N.Y. Plasmid ColE1 is described in Bazarel et al., 1968, Biochem.7, 3513–3517. One of skill in the art will appreciate that any origin of replication may be provided y isolating the appropriate restriction fragment from any plasmid known in the art.

Plasmid pMB1 is described in Betlach et al., 1976, Fed. Proc. 35, 2037–2043. Derivatives of ColE1 and pMB1, like the parent plasmids, are multi-copy plasmids. ColE1 and pMB1 are maintained at about 10–25 copies per chromosome equivalent. An approximate 580 bp sequence of ColE1 and pMB1 is required for plasmid DNA replication (Betlach et al., 1976, Fed. Proc. 35, 2037–2043). The Pst1-BamH1 fragment of pBR328 contains the ColE1 origin of replication (Soberon et al., 1980, Gene 9, 287–305). Both the origin of replication and the information for regulation of initiation of replication from this origin are contained within this sequence (Tomizawa et al., 1975, Proc. Nat. Aca. Sci. 72, 1050–1055; Donoghue et al., 1978, J. Bacteriol. 133, 1289–1294, Inuzuka et al., 1978, Proc. Nat. Aca. Sci. 75, 5381–5385). No plasmid-encoded proteins appear to be involved in replication of ColE1 or ColE1-derived plasmids. Among the many derivatives of ColE1 or pMB1, plasmid pBR322 is the most commonly employed vehicle for cloning in *E. coli*. An approximate 1. 6 kb PvuII-Pst1 fragment or a 2.0 kb PvuII-Ball fragment of pBR322 contains the origin of replication. The sequence of pBR322 is provided in Sutcliffe, 1979. Cold Spring Harbor Symp. 43, 77–90. The pUC plasmids, containing the lac promoter, contain a pMB1 origin of replication, which is located on an approximate 1.0 kb PvuII-Pst1 fragment. p15A (Cozzarelli et al., 1968, Proc. Nat. Aca. Sci. 60, 992–999) is a ColE1-related plasmid are present in somewhat lower copy number than pMB1 plasmids, i.e., at about 3–5 copies per chromosome equivalent.

Host Cells Useful According to the Invention.

The invention is applicable to all cell types including animal cells such as mammalian and insect cells, plant cells, fungi such as yeast, and most strains of bacteria, for example, gram positive and negative bacterial strains, provided a plasmid exists that is capable of being maintained in the host cell at a medium to high copy number.

Gram negative bacteria useful according to the invention include but are not limited to *E. coli* and Salmonella, e.g., *S. typhimurium*.

Gram positive species useful according to the invention include but are not limited to Bacillus, Streptomyces, Lactobacillus and Lactococcus, for which high copy number plasmids already exist. Examples of plasmids useful according to the invention in Lactococcus are pNZ2123 and pIL253 (Simon et al., Biochimie 70:559, 1988)). The lactococcal lactose operon has been used to control the expression of heterologous proteins (Wells et al., 1993, Mol. Microbiol. 8(6):1155–1162). This operon utilizes the lacR repressor (van Rooigen et al., J. Biol. Chem. 265:18499–18503, 1990) to control the expression of T7 polymerase, which then controls the expression of the heterologous protein. Examples of plasmids useful according to the invention in Bacillus are pC 194, pUB110 and pT181.

In Bacillus, e.g., *B. mibtilis*, the $\lambda$ repressor has been used to control the expression of heterologous proteins. The $\lambda$ repressor has been placed under the control of the sak42D promoter, which can be efficiently transcribed in *B. sibtilis* (Breitling et al., 1990, Gene 93(1):35–40).

Yeasts are useful according to the invention, as high copy number plasmids are maintained in yeasts. Examples of such plasmids include the YRp plasmids (based on autonomously replicating sequences (ARS)) which have copy numbers up to about 100 copies per cell, and the YEp plasmids (based on the 2 micron circle), with a copy number of 50–100 per cell. (See Sikorski, "Extrachromosomal cloning vectors of Saccharomyces cerevisiae", in Plasmids, A Practical Approach, Ed. K. G. Hardy, IRL Press, 1993; and Yeast Cloning Vectors and Genes, SectionII, Unit 13.4, Current Protocols in Molecular Biology, Eds., Ausubel et al., 1994.) Yeasts are able to express the *E. coli* lacZ gene, it is therefore contemplated according to the invention to use the lac repressor titration system to control the expression of essential yeast genes such as ura3 or leu2, genes which have been used for the maintenance of plasmids in yeasts (Gunge, 1983, Ann. Rev. Micro. 37:253–276).

When the host cell is a eukaryotic cell, the Lac and Tet repressors and their corresponding operators are preferably used. The use of Lac and Tet repressors to regulate gene expression in eukaryotic cells, including yeast, dictiostelium, plants cells and tobacco plants is described by Gossen et al ((1994) Current Opinions in Biotechnology, 5, 516–520).

Essential Genes Useful According to the Invention.

The invention may be used in conjunction with a number of different essential chromosomal host genes for the stable maintenance of the plasmid. These essential genes include but are not limited to the following categories, e.g., genes encoding products related to the biosynthesis of cell metabolites, genes whose products are involved in carbon metabolism, genes coding for antibiotic resistance, and genes encoding the biosynthesis or regulation of macromolecules, e.g., genes essential for DNA and/or RNA synthesis and replication functions.

1. Essential Genes Encoding Products Related to Synthesis of Components of Cell Structure.

Certain genes encoding enzymes involved with the supply of cell components, in particular the supply of cell wall precursors, are also essential for host cell growth and are useful according to the invention. For example, the bacterial cell wall contains meso-diamiopimelic acid (DAP), and an inability to synthesize this component results in cell lysis. It has been demonstrated that mutants in which the asd gene (aspartate $\beta$-semialdehyde dehydrogenase) or dapD gene (succinyl diaminopimelate aminotransferase) are deleted can be used for the maintenance of plasmids that carry a complete copy of that gene on the plasmid. (Nakayama et al., Bio/technology 6:693–697, 1988; DeGryse, U.S. Pat. No. 5,198,343). A number of other genes in the DAP biosynthetic pathway could also be used, namely dapA, dapB, dapC and dapE genes. dapA and dapB have been cloned and sequenced, and dapB is available as a single cistron (Richaud et al., J. Bacteriol. 166:297–300, 1986; Bouvier et al., J. Biol. Chem. 259:14829–14834, 1984). The genes involved in the biosynthesis of other cell wall components, such as D-alanine biosynthesis, are also useful according to the invention (Walsh, 1989, J. Biol. Chem. 264(5):2393–2396). A DNA sequence encoding a component for D-alanine has been used for the stabilization of plasmids without using antibiotics (see EP 85/309020).

The invention contemplates the use of repressor titration in conjunction with such genes. The gene of interest is first deleted from the host strain such that the host now has a requirement for the product of that gene (Winans et al., 1985, J. Bact. 161(3):1219–1221; Jasin et al., 1984, J. Bact. 159(2):783–786). A copy of the gene is constructed using conventional cloning techniques so that its expression is directed by the, promoter/operator which binds the chosen repressor protein. This construct is then introduced into the chromosome of the host strain which synthesizes the repressor protein (Winans et al., 1985, J. Bact. 161(3):1219–1221; Jasin et al., 1984, J. Bact. 159(2):783–786). Transformation of the strain with a plasmid containing the repressor binding sequence results in titration of the repressor away from the biosynthetic gene, enabling expression of the essential gene.

2. Genes Essential for Cell Growth.

The repressor-titration method of the invention can be used with genes involved with the utilization of carbon sources. Specifically, the method can be used with the lactose operon and the utilization of lactose as the sole carbon source, as described herein. Other modifications will be apparent to one of skill in the art. Mutants of the lac repressor exist that are no longer able to bind the inducer (allolactose) and remain bound to the lac operator in normal inducing conditions. These are typified by the lacI$^s$ mutants; however, other mutations exist that have no capacity to bind inducer but are normal in all other functions (Chang et al., Biochem. 33:3607–3616 (1994)). Strains carrying these mutations would not be able to express the genes of the lac operon and hence not be able to grow with lactose as the sole carbon source. Transformation of such strains with high copy number plasmids containing wild type lac operator sequences will titrate the repressor away from the lac operon and allow growth on lactose.

Glutamine synthetase is an essential gene for eukaryotic cells such as the NSO myeloma cell line (Bebbington et al., (1992) Bio/Technology 10, 169–175) and is preferably used when the host cell is a eukaryote cell.

3. Genes Encoding the Synthesis of Nucleic Acids.

The invention can also be used in conjunction with essential genes encoding DNA and/or RNA synthesis or replication proteins of the host cell. Examples of such genes with respect to these essential functions in bacteria such as *E. coli* and Salmonella are provided in McMacken et al. (in *Escherichia coli* and *Salmonella typhimurium*, Cellular and Molecular Biology, Ed. Neidhardt et al., Amer. Soc. Micro., Wash. D.C., 1987, pp. 564–612), and include but are not limited to the following genes: dnaA, dnaB, dnaC, ssb, dnaG, polC (dnaE), dnaQ (mutD) dnaN, dnaZX, gyrA, gyrB, polA, lig, dnaT, rpoA, rpoB, rpoC, and rpoD.

4. Genes Encoding Antibiotic Resistance.

The invention can also be used in conjunction with antibiotic resistance. The resistance gene is constructed such that its expression is under the control of the promoter/operator that binds the desired repressor protein. This construct is then inserted into the chromosome of the host strain. Transformation of the strain with plasmid containing the repressor binding sequence will titrate the repressor from the antibiotic resistance gene and allow expression and hence growth in the presence of that antibiotic. An antibiotic resistance gene is such a useful selectable marker that a practitioner of the invention might choose antibiotic resistance as the host essential gene even though attention would have to be paid to purifying the plasmid product away from the antibiotic used in the scale-up fermentation process.

In Example I, the invention is applied using the lac repressor/operator system in experiments which demonstrate the ability of plasmid borne sequences to titrate repressor away from the chromosomal gene.

EXAMPLE I

*E. coli* strain DH1 (Hanahan, J. Molec. Biol. 166:557–580, 1983) possesses an intact lactose operon which is subject to control by the lactose repressor protein (LacI). LacI is present at 10–20 copies per cell and binds with high affinity (kd 1×10–14).

*E. coli* DH1 was transformed with pUC18tet (a pUC18 based plasmid containing ampicillin and tetracycline resistance genes that is present at approximately 100–200 copies per cell). pUC 18tet contains the lac operator/promoter but does not contain LacI gene encoding the repressor protein. The plasmid also contains the pUC origin of replication and a polylinker (or multiple cloning site) for insertion of a therapeutic gene. Plasmid-encoded ampicillin and tetracycline resistance is not necessary for repressor titration, and a plasmid containing no antibiotic resistance is preferred according to the invention, and may be readily substituted for pUC 18tet.

DH1 and DH1:pUC18tet were grown on M9 minimal salts medium with lactose (10 mM) or glucose (10 mM) as carbon sources supplemented with ampicillin (50 μg/ml) where necessary. Cells were harvested during log growth and assayed for β-galactosidase activity (Miller, 1972, Experiments in Molecular Genetics, Cold Spring Harbor Laboratory, CSH, NY). As shown in Table 1, comparable β-galactosidase activities are observed with DH1:pUC18tet grown on glucose and lactose whereas very much lower activities are seen with DH1 grown on glucose compared to lactose. The presence of the plasmid, therefore, titrates the lac repressor away from the lac operon, allowing the expression of β-galactosidase.

TABLE 1

Expression of β-galactosidase in *E. coli* DH1 in the presence and absence of pUC18tet when grown under inducing and non-inducing conditions

|  | DH1 Activity (units) | % | DH1::pUC18tet Activity (units) | % |
| --- | --- | --- | --- | --- |
| Experiment 1 |  |  |  |  |
| Lactose | 1391 | 100 | 4162 | 300 |
| Glucose | 27 | 2 | 120 | 224 |
| Experiment 2 |  |  |  |  |
| Lactose | 2571 | 100 | 7140 | 277 |
| Glucose | 9 | 0 | 6466 | 255 |
| Experiment 3 |  |  |  |  |
| Lactose | 1123 | 100 | 1400 | 125 |
| Glucose | 29 | 2.5 | 1157 | 103 |

Results are of three independent experiments and are expressed as units and as a percentage of value obtained for lactose grown DH1 for each experiment.

EXAMPLE II

The following example demonstrates repressor titration.

*E. coli* strain Hfr 3000 YA 694 (CGSC 6378)lacI694, relA1, spoT1,thi-1, λ, was plated onto EMB agar and grown overnight, resulting in pink colonies indicating that the strain is unable to ferment lactose and has the lacI$^s$ genotype, i.e. encodes a repressor which is inducer insensitive (Wison et aL, (1964) J. Mol. Biol, 8: 582). A single colony was grown and made competent for transformation. This strain was then transformed with pUC18 (which contains the lac operator and is described above) and plated onto EMB agar containing ampicillin. The resulting colonies were black indicating that lactose was fermented as a result of the lacI$^s$ repressor being titrated away from the lac operon allowing expression of the β galactosidase gene. A single colony was inoculated into 5 ml of LB ampicillin and grown to mid log and shown to express β-galactosidase activity.

E.coli strain Hfr 3000 YA694 untransformed and transformed with pUC18 was plated onto minimal medium containing lactose as the sole carbon source supplemented with ampicillin where applicable. It can be seen in FIG. 3 that the introduction of pUC18 resulted in the ability to grow on lactose.

EXAMPLE III

The following example demonstrates plasmid maintenance by repressor titration.

E.coli strain YA694 containing pUC18 was inoculated into 5 ml M9 minimal medium supplemented with glucose (0.1 g/l) ampicillin (50 μg/ml) and thiamine (0.5 mg/l) and grown at 37° C. for 14 h. 0.5 ml of this culture was then inoculated separately into:

(1) 100 ml of M9 medium supplemented with glucose,
(2) 100 ml M9 medium supplemented with lactose,
(3) 100 ml M9 medium supplemented with lactose and ampicillin.

The cultures were then grown for approximately 8 h at 37° C. OD600 measurements were taken throughout the growth period. 2 OD units were removed at the end of the growth period, harvested and frozen. 0.5 ml of each culture was then inoculated into 100 ml fresh respective medium and grown for a further 14 h. The procedure was then repeated to achieve approximately 72 generations of growth with samples being taken at appropriate growth points.

Figure 4A:
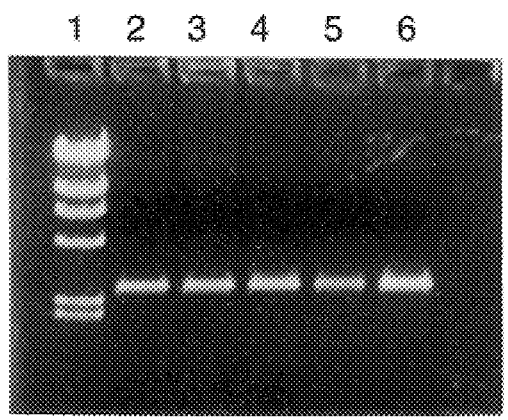
FIG. 4 is an agarose gel in which plasmid DNA has been electrophoresed, the plasmid DNA having been prepared from cells grown on minimal medium containing glucose plus ampicillin and then inoculated into minimal medium containing a) lactose and ampicillin, b) lactose, c) glucose; wherein lane 1 includes λ HindIII standards, lane 2, EcoRI-restricted inoculum plasmid DNA, lanes 3–6, Eco RI-restricted plasmid DNA isolated after growth for approximately 15, 36, and 72 cell generations, respectively.
Figure 4B:
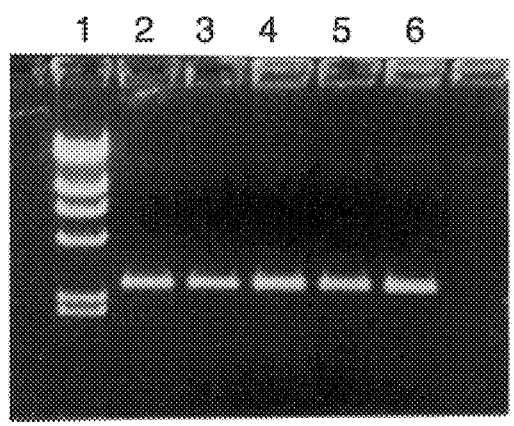
Figure 4C:
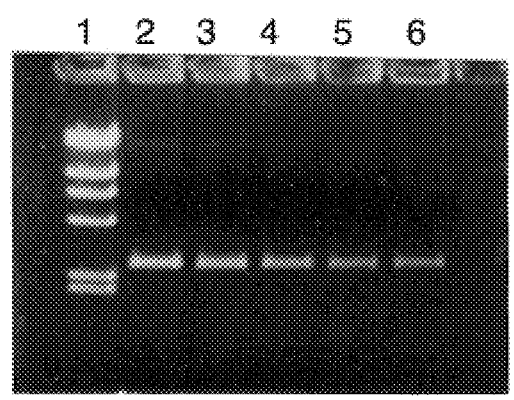

Plasmid DNA was then isolated from the harvested cells digested with EcoRI and analysed by gel electrophoresis. The results indicate that after 72 generations of growth the plasmid was present at a higher specific yield in cells grown on lactose alone than in cells grown in glucose alone (FIG. 4). This demonstrates that by making growth dependent on the production of β, galactosidase to metabolise lactose, the plasmid, which allows expression of the β galactosidase gene, is selectively maintained.

EXAMPLE IV

The following example demonstrates alternative repressors.

The ability of the mutant repressor ArgRNV to act as a repressor that can be used in the repressor titration system was investigated. ArgRNV, a genetically engineered mutant of ArgR (Burke et aL, 1994, Mol. Microbiol. 13(4), 609–618), remains bound to its DNA binding site within the promoters of the arginine biosynthetic genes even in the absence of arginine. Transformation of E. coli strains DS997 and DS998 with the ArgRNV gene on a multi copy plasmid has been shown to prevent growth in minimal medium (Burke et al., 1994, Mol. Microbiol. 13(4), 609–618). The repressor therefore exhibits transdominance. The experiment described in Example I was repeated with E. coli DH1, which was transformed with ArgRNV encoded on a high copy number plasmid (pSelect, Promega), subsequent growth on minimal medium occurred only in the presence of arginine demonstrating the ability of the repressor to be used in a repressor titration system.

In order to demonstrate plasmid maintenance via a chromosomally encoded ArgRNV repressor, the ArgRNV is then placed into the chromosome of DH1 and the ability to prevent growth in minimal medium tested as described in Example I. The ability of plasmids containing the ArgR binding site to titrate the ArgRNV away from the arginine biosynthetic genes or from an essential gene functionally associated to the Arg operator is then tested as described in Example I.

EXAMPLE V

The following example demonstrate generation of a representative essential gene.

An in-frame fusion of the N-terminal region of the lacZ gene and the kanamycin gene to be used as a model of an essential gene under the control of the lac operator/promoter was constructed in the following manner (the kanamycin gene can be substituted by any essential gene). The kanamycin cassette was removed from pUC4 K (Pharmacia Biotech) by digestion with XhoI and PstI, this was ligated into pUC18 which had been digested with SalI and PstI. This created a functional in frame fusion of the lacZ gene with the kanamycin gene, such that expression of kanamycin resistance was under the control of the lac operator promoter.

Figure 5:
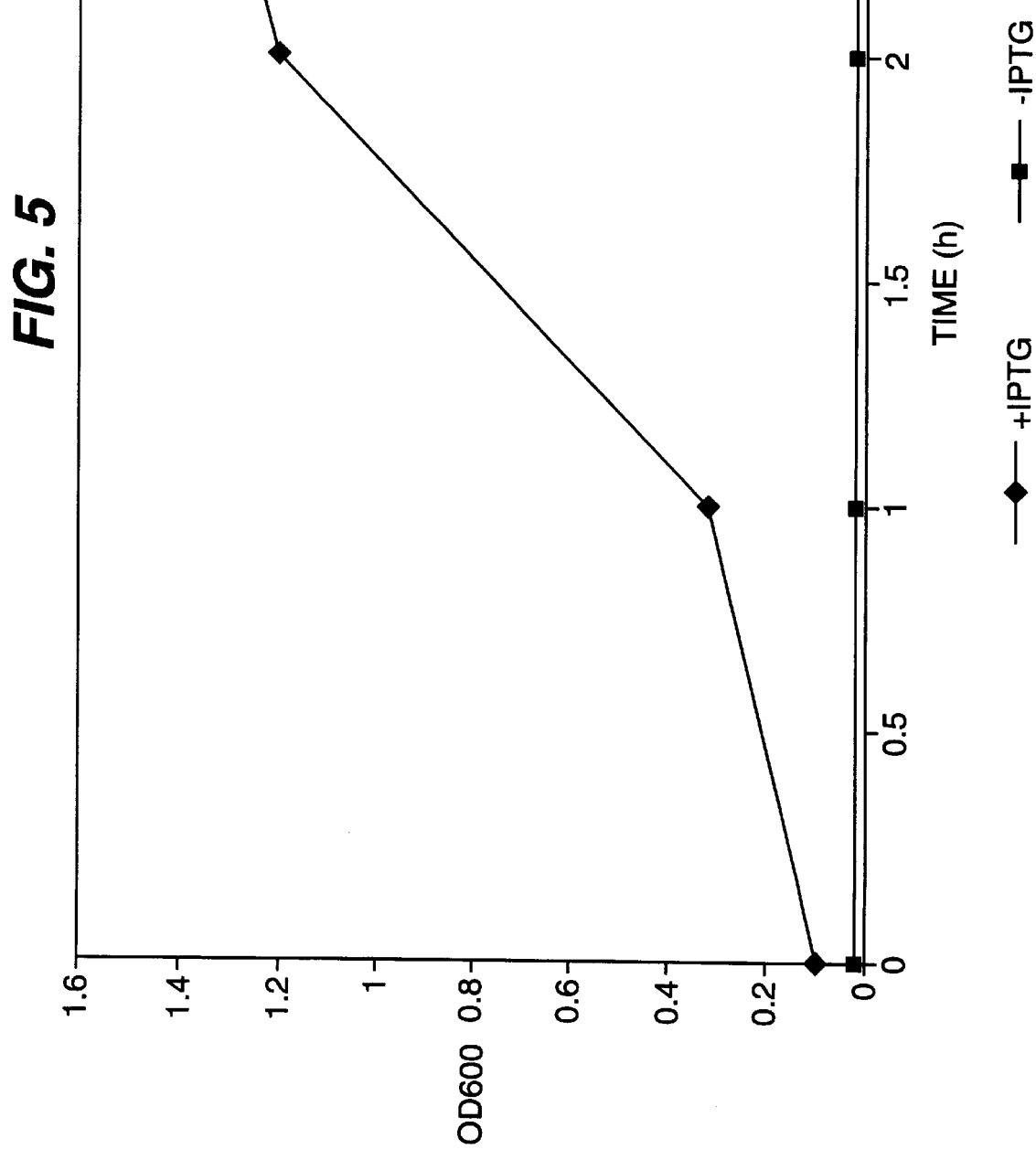
FIG. 5 shows the derepressible growth of JC7623 lacZ-kan in the presence of kanamycin.

The lacA/kanamycin construct was isolated by digestion with HaeII, blunted and ligated into pnN1 which had been digested with StyI and blunted. pnN1 is a pUC18 based plasmid containing 5.5 kb of E. coli chromosomal DNA surrounding the dif locus (Leslie et al., 1995, Eur. J. Mol. Biol. 14, 15 61–1570). Insertion of the lac/kanamycin into the dif locus of pnN1 ultimately allows recombination of the construct into chromosome of the desired E. coli host. The resulting plasmid was linearized with SalI and used to transform E. coil JC7 623 (Winans et al., 1985, J. Bact., 161(3), 1219–1221) and selected on kanamycin +IPTG plates. Kanamycin resistant clones were tested for IPTG inducibility of growth in the presence of kanamycin (FIG. 5), the loss of plasmid, and the insertion of the construct into the chromosome by Southern analysis.

Figure 6:
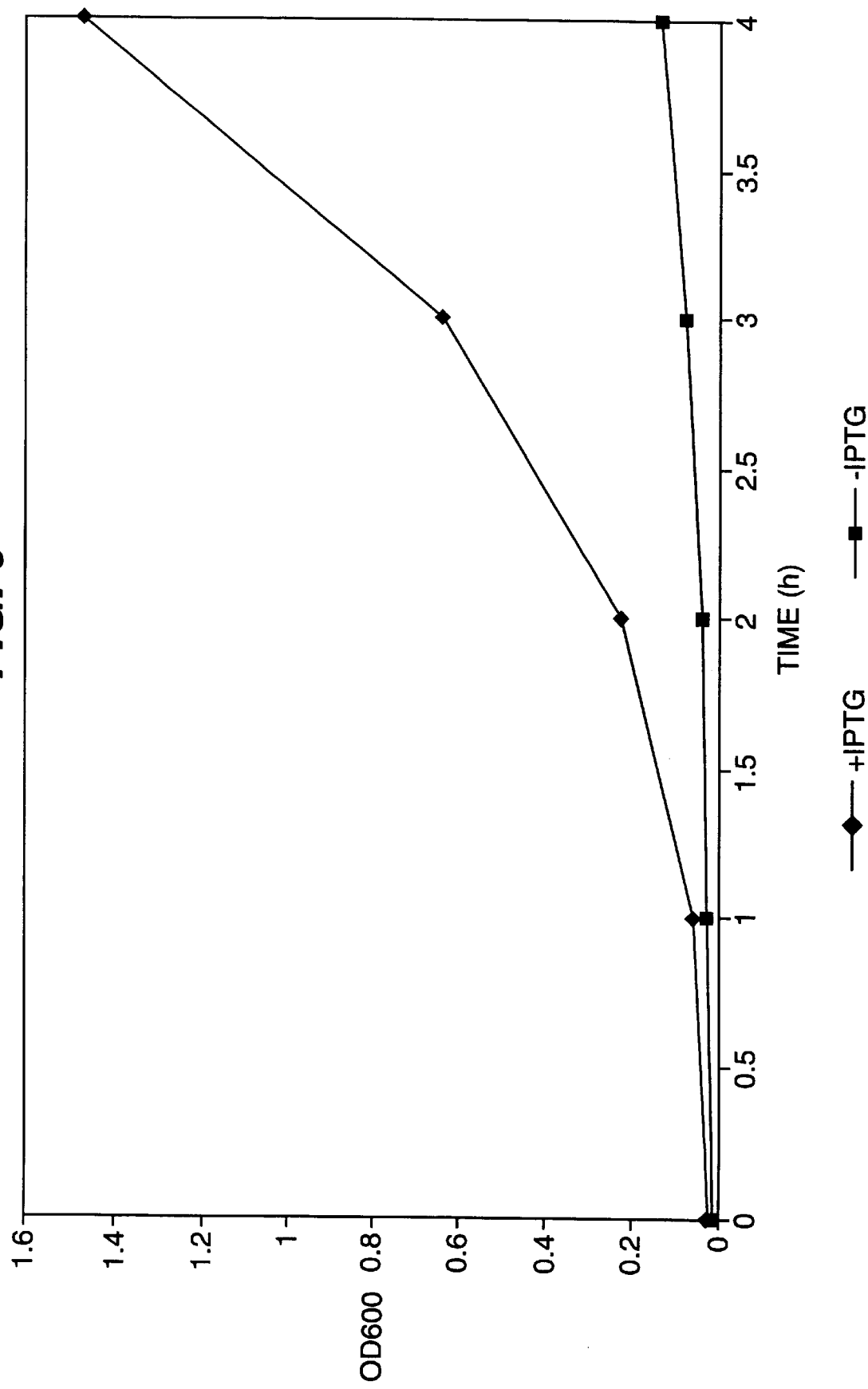
FIG. 6 shows the derepressible growth of DH1 lacZ-kan in the presence of kanamycin.

The construct was then transferred from the chromosome of JC7623 into the chromosome of DH1 by means of P1 transduction. The resulting DH1 lac/kan strain was analysed by Southern analysis for the presence of the construct within the dif locus and the inducibility of kanamycin resistance (FIG. 6). Transfection of DH1 lacZ-kan with pUC18 Tet results in growth in the presence of kanamycin without IPTG, demonstrating repressor titration wherein the kanamycin resistance gene is repressed, and the host cell grows in the presence of kanamycin.

The DH1 lac/kan strain was then transformed with a number of plasmids possessing the lac operator (pUC18, pUC18tet and larger plasmids derived from these) and tested for:

1. Growth on medium containing kana/mnycin (60 μg/ml) under non-inducing conditions;
2. The maintenance of plasmid during batch growth by means of the repressor titration system.

Titration of the lac repressor away from the lac/kanamycin construct was demonstrated and maintenance of the plasmid during batch growth was also demonstrated.

EXAMPLE VI

The following example demonstrates how to provide a host cell containing an essential gene under the control of the lac operator/promoter. A lacZdapD gene fusion was constructed and inserted into the dif locus of an E. coli DH1 dapD-strain. It will be appreciated by one of skill in the art that modifications can be made to the constructs described herein, including for example modifications to the various control sequences described herein.

A lacZdapD fusion was constructed as follows.

The dapD gene was cloned from DH1 by PCR using primers into which EcoRI sites had been engineered (5'GTGCCCGAATTCCAATTGGCG-3'SEQ ID NO: 1, 5'-CGGCGTGAATTCATCGCTCATCCC-3'SEQ ID NO:2). The PCR product was digested with EcoRI and ligated into EcoRI digested pUC18. The resulting plasmid (pUC18dapD) was used to transform E. Coli strain AT982 (dapD4, thi1, relA1, λ-, spoT1) and shown to complement the dapD mutation demonstrating that the dapD gene had been cloned. A fusion of the dapD gene with the lacZ gene of pUC18 was then created by PCR utilizing pUC18dapD and the oligonucleotides: 5'-CAATGCAGAATTCACAGAACATTA-3'SEQ ID NO:3 and 5'-CGGCGTGAATTCATCGCTCATCCC-3'SEQ ID NO:4.

Digestion with EcoRi and ligation into pUC18 that had also been digested with EcoRI created an in-frame fusion between the lacZ and the dapD genes. This construct (pUC18dapD2) was shown to be functional again by the restoration of growth of AT982 after transformation. The lac/dapD fusion was isolated as a HaeII fragment, blunted and ligated into pN1 that had been digested with Sty1 and then blunted. This plasmid (pN1 dap D2) complemented the dapD mutation in strain AT982.

Inactivation of the WT DH1 dapD gene.

Before the insertion of the lacZdapD fusion into the chromosome of DH1, expression of the WT gene was first inactivated. The dapD gene was recloned by PCR with larger fragments of DNA 5' and 3' to the dapD gene using the oligonucleotides:

```
5'-TCATCGGAATTCCCTGGAGTATCGG-3'   and   SEQ ID NO:5

5'-TGAGCTGAATTCCATCGCCGCGCTG-3',         SEQ ID NO:6
``` to allow more efficient recombination. The resulting PCR product was digested with EcoRI and ligated into pUC18 in which the PsiI site had been deleted. The resulting plasmid (pUC18 dapD3) complemented the dapD mutation in AT982.

The dapD gene was then insertionally inactivated by the introduction of the kanamycin cassette from pUC4 K into the PstI site located within the dapD gene. This plasmid (pUC18dapDkan) no longer complemented the dapD mutation in AT982. The construct was introduced into the chromosome of E. coli JC7623 by transformation with pUC18dapDkan which had been linearized by digestion with BamHI. Clones were screened for the inability to grow in the absence of supplementary diaminopimelate but the ability to grow in the presence of kanamycin. The presence of the kanamycin gene within the dapD gene was confirmed by Southern analysis. The inactivated dapD gene was then transferred into the chromosome of DH1 by P1 transduction to produce DH1 dapDkan.

Figure 7:
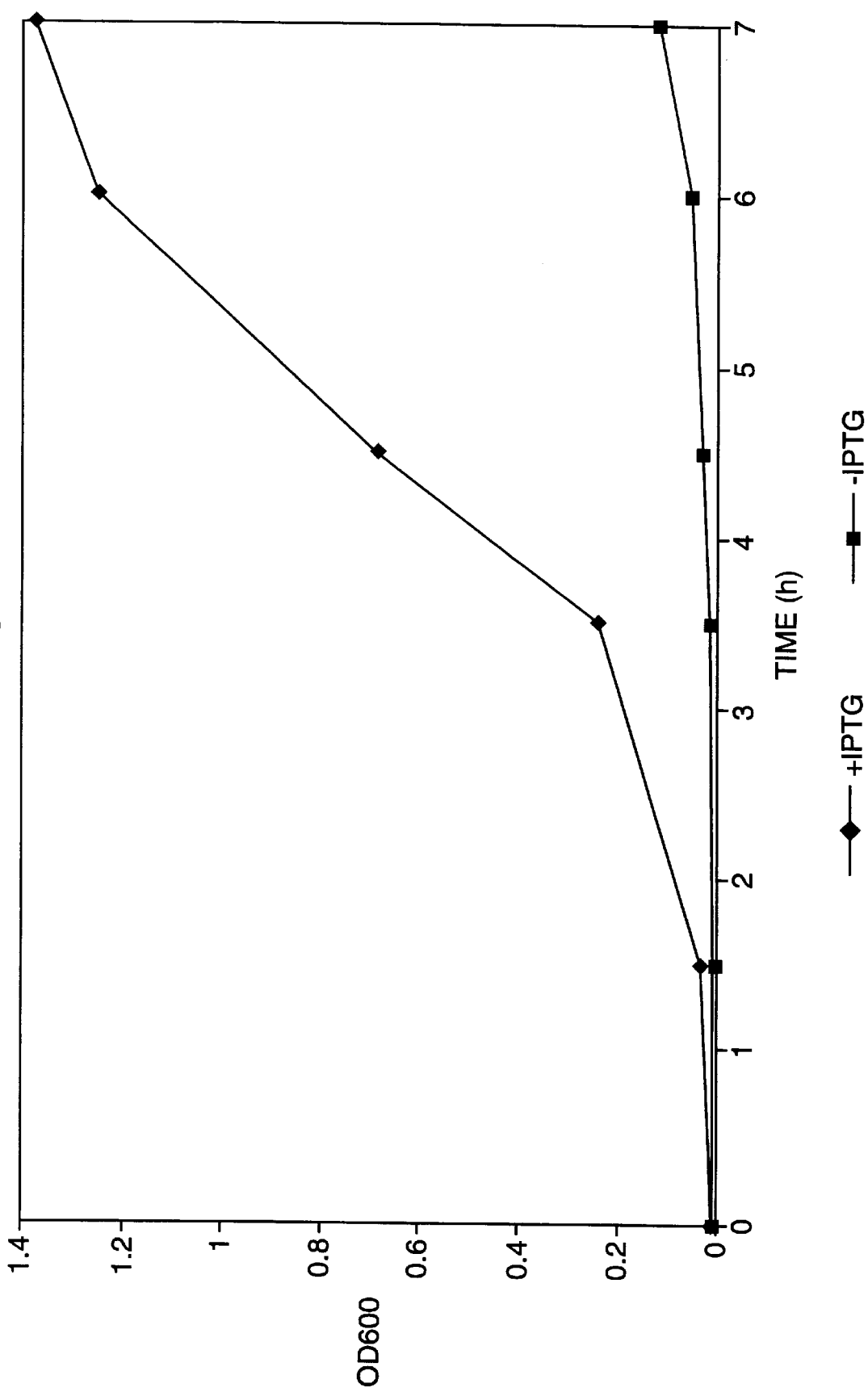
FIG. 7 shows the derepressible growth of JC7623 dapD-kan lacZ-dapD in the absence of diamninopimelate.

The lacZdapD construct was introduced into the chromosome of JC7623dapDkan by transformation with pN1dapD2 that had been linearized with ScaI. Clones were isolated and the IPTG inducement of growth in the absence of diamonopimelate was then demonstrated (FIG. 7).

The lac/dapD fusion was then introduced into DH1dapDkan by means of P1 transduction and screened for IPTG inducible growth and its location within the dif locus confirmed by Southern analysis.

The DH1 dapDkan-lacdapD strain was then transformed with plasmid possessing the lac operator (pUC18Tet) and the following characteristics demonstrated:

1. Growth of DH1 dapDkan-lacdapD on medium lacking diaminopimelate under non inducing conditions, demonstrating titration of the lac repressor away from the lac/dapD construct;
2. The maintenance of the plasmid was tested during batch growth and plasmid yields compared with cells grown in the presence of tetracycline (i.e. to select for the plasmid by means of the antibiotic resistance gene) and cells grown in the presence of an inducer (IPTG) (i.e. conditions where maintenance of the plasmid is not required). The specific yield of plasmid in the absence of tetracycline was comparable to that observed in the presence of tetracycline, thus demonstrating the selective maintenance of the plasmid in the absence of antibiotics. in both cases the yield was significantly greater than for cells grown in the presence of an inducer.

EXAMPLE VII

Plasmid DNA stably maintained in a host cell according to the invention is isolated as follows. Cells are lysed and plasmid DNA purified according to methods well known in the art, and as described in Brinboim et al., 1979, NAR 7:1513–1523, and Bimboim, 1983, Methods Enzymol. 100:243–255, or using a Qiagen plasmid mini, maxi, or mega kit (Qiagen, Chatsworth, CA). For large-scale purification of plasmid DNA, e.g., 100 mg or greater, see Horn et al., 1995, Human Gene Therapy 6:565–573.

EXAMPLE VIII

Where a gene of interest encoding a recombinant protein is carried on the plasmid such that it is under control of host cell regulatory sequences (i.e., minimally, a promoter that functions in the host cell), the recombinant protein may be produced during cell growth and then isolated according to methods known in the art, as follows. Production and purification of recombinant proteins in E. coli is accomplished as described in Das,1990, "Overproduction of proteins in E. coli: Vectors, host and strategies", Methods in Enzymol. 182:93–112; Marston et al., 1990, "Solubilization of protein aggregates", Methods in Enzymol. 182:264–276; and Thatcher et al., 1994, "Protein folding in biotechnology", in Mechanisms of Protein Folding, Ed. R. H. Pain, Frontiers in Molecular Biology Series, IRL Press, Oxford University, UK.

Production and purification of soluble and/or periplasmic recombinant proteins in E. coli may be performed as described in Hart et al., 1994, Bio/Technology 11:1113–1117; Schein, 1989, Bio/Technology 7:1141–1149; and Lavallie et al., 1993, Bio/Technology 11:187–193.

Production and purification of recombinant proteins in S. cerevisiae may be performed as described in Romanos et al., 1992, "Foreign gene expression in yeast; a review", in Yeast 8:423–488.

Production and purification of recombinant proteins in yeast Phichia pastoris may be performed as described in Sreekrishna et al., 1989, Biochemistry 28:4117–4125.

Production and purification of recombinant proteins in mammalian cells may be performed as described in Reff, 1993, Curr. Opin. Biotech. 4, 573–576, or in Cartwright, 1994, Animal Cells as Bioreators, Cambridge Studies in Biotechnology 11, Cambridge University Press.

USE AND ADMINISTRATION

Plasmid DNA produced according to the invention is useful in gene therapy when the plasmid contains a therapeutic gene. A therapeutic gene is one which is expressible in a mammalian, preferably a human, cell and encodes RNA or a polypeptide that is of therapeutic benefit to a mammal, preferably a human. Examples of such genes are well known in the art and include but are not limited to the β-glucocerebrosidase gene, the Bruton's thymidine kinase gene, genes encoding cytokines, such as TNF, interleukins 1–12, interferons (α,β, γ), Fc receptor, T-cell receptor, and p53. Other examples include genes encoding inhibitors of HIV, e.g., TAT or REV mutants that act as competitive inhibitors of the natural proteins. The plasmid DNA may also include marker genes, such as drug resistance genes, the β-galactosidase gene, the dihydrofolate reductase gene, and the chloramphenicol acetyl transferase gene.

Use of such DNA in vivo or ex vivo where the therapeutic gene encodes a product of physiological importance, such as replacement of a defective gene or an additional potentially beneficial gene function, is expected to confer long term genetic modification of the cells and be effective in the treatment of disease.

Plasmid DNA containing a therapeutic gene is administered using a viral or non-viral mode of in vivo or ex vivo gene therapy. The mode of administration is not critical to the invention, and may include the use of a gene gun for administration of naked DNA, receptor mediated gene therapy, e.g., using liposome/antibody complexes, and viral vectors.

For example, a patient that is subject to a viral or genetic disease may be treated in accordance with the invention via in vivo or ex vivo methods. For example, in in vivo treatments, plasmid DNA of the invention can be administered to the patient, preferably in a biologically compatible solution or a pharmaceutically acceptable delivery vehicle, by ingestion, injection, inhalation or any number of other methods. The dosages administered will vary from patient to patient; a "therapeutically effective dose" will be determined by the level of enhancement of function of the transferred genetic material balanced against any risk or deleterious side effects. Monitoring levels of gene introduction, gene expression and/or the presence or levels of the encoded product will assist in selecting and adjusting the dosages administered. Generally, a composition including a delivery vehicle will be administered in a single dose in the range of 10 ng–100 ug/kg body weight, preferably in the range of 100 ng–10 ug/kg body weight, such that at least one copy of the therapeutic gene is delivered to each target cell.

Ex vivo treatment is also contemplated within the present invention. Cell populations can be removed from the patient or otherwise provided, transduced with a plasmid containing a therapeutic gene in accordance with the invention, then reintroduced into the patient.

The cells targeted for ex vivo gene transfer in accordance with the invention include any cells to which the delivery of the therapeutic gene is desired, for example, cells of the immune system such as T-cells, B-cells, and macrophages, hematopoietic cells, and dendritic cells. Using established technologies, stem cells may be used for gene transfer after enrichment procedures. Alternatively, unseparated hematopoietic cells and stem cell populations may be made susceptible to DNA uptake as described herein.

Two representative plasmids are described below for treatment of human genetic diseases. A plasmid according to the invention may be used to treat X-linked β-globulinemia. This plasmid will contain the minimal sequences described herein, i.e., an origin of replication for replication in a bacterial or yeast host cell, an operator sequence, and a site for insertion of a therapeutic gene. For example, the pUC18tet plasmid may be used as a minimal plasmid, preferably with the tet gene deleted. The therapeutic gene may be the Bruton's kinase gene (Vetrie et al., 1993, Nature 361:226–233), and is carried on the following DNA fragments, which are cloned together using procedures well-known in the art. The Bruton's Tyrosine Kinase human gene is carried on a 2.1 kb fragment delineated by the PvuI site at position (+33) and the HindIII site at position (+2126). If desired, the plasmid also may include sequences which confer position independent, tissue specific gene expression, as taught in PCT/GB88/00655. The therapeutic gene may also encode a splice site and poly A tail, which may include portions of the human β globin locus splice and poly A signals; i.e., a BamHI-XbaI 2.8 kb 3' splice/poly A flanking sequence containing exon 2-IVSII-exon 3-polyA sequences.

Plasmid DNA may be prepared as described herein and used to treat X-linked β-globulinemia by introducing the construct directly into a patient for in vivo gene therapy or into pre-B cells for ex vivo therapy, as described in Martensson et al., Eur. Jour. Immunol. 1987, 17:1499; Okabe et al., Eur. Jour. Immunol. 1912, 22:37; and Banerji et al., Cell 33:729, 1983, and administering the transfected pre-B cells into a patient afflicted with X-linked β-globulinemia.

Plasmid DNA prepared according to the invention also may be used for treatment of Gaucher's disease. Gaucher's disease stems from one of two different genetic mutations. Gaucher's type 1 is a CGG—>CAG mutation, which results in an Arg—>Gin substitution at position 119 of the β-glucocerebrosidase polypeptide (Graves, DNA 7:521, 1988). Gaucher's type 2 is a CTG—>CCG mutation, which results in a Leu—>Pro substitution at position 444 of the β-glucocerebrosidase polypeptide (Tsuji, NEJM 316:570, 1987). The presence of a β-glucocerebrosidase gene encoding a wild type polypeptide is believed to substantially correct Gaucher's disease. Therefore, another plasmid useful according to the invention is one containing the minimal elements described herein (i.e., an origin of replication, an operator sequence, and a cloning site) and the lysozyme gene promoter and the β-glucocerebrosidase transgene, as described in Horowitz et al., 1989, Genomics 4:87–96. This plasmid is constructed as follows.

The human β-glucocerebrosidase gene is carried, as disclosed in Horowitz et al., on a 9722 base pair fragment extending from a BamHI site in exon 1 to an EcoRV site 3' to polyadenylation site. This fragment contains 11 exons and all intervening sequences, with translational start in exon 2. Sequences conferring position-independent and tissue-specific gene expression may be included in the construct and are carried on an 11.8 kb XhoI -SacI fragment from pIII.lyx construct as described in Bonifer et al., 1990, Euro. Mol. Biol. Org. Jour. 9;2843.

Plasmid DNA is prepared as described herein and is then used to treat Gaucher's disease by introducing the DNA directly into the host for in vivo treatment, or into macrophages for ex vivo therapy, as described in Immunology and Cell Biology, 1993, Vol. 71, pages 75–78 and introducing the transfected macrophages into a patient afflicted with Gaucher's disease. Expression of the wild type transgene in a patient afflicted with Gaucher's disease should result in correction of the diseased state.

OTHER EMBODIMENTS

Other embodiments will be evident to those of skill in the art. It should be understood that the foregoing detailed description is provided for clarity only and is merely exemplary. The scope of the present invention is not limited to the above examples, but is defined by the following claims.

We claim:

1. A transformed host cell containing
   a) a plasmid comprising an operator that binds to a repressor;
   b) a first chromosomal gene encoding said repressor; and
   c) a second chromosomal gene that is functionally associated with said operator and essential for cell growth, wherein said plasmid is present in said cell in sufficient numbers to titrate said repressor such that said essential gene is expressed, thereby permitting cell growth, provided that said second chromosomal gene is not an antibiotic resistance gene.

2. A transformed host cell containing
   a) a plasmid comprising an operator that binds to a repressor;
   b) a first chromosomal gene encoding said repressor; and
   c) a second chromosomal gene that is functionally associated with said operator and essential for cell growth, wherein said plasmid is present in said cell in sufficient numbers to titrate said repressor such that said essential gene is expressed, thereby permitting cell growth, and wherein said second chromosomal gene is required for the biosynthesis or metabolism of a cell metabolite or for DNA and/or RNA synthesis and replication functions.

3. A transformed host cell containing
   a) a plasmid comprising an operator that binds to a repressor;
   b) a first chromosomal gene encoding said repressor; and
   c) a second chromosomal gene that is functionally associated with said operator and essential for cell growth, wherein said plasmid is present in said cell in sufficient numbers to titrate said repressor such that said essential gene is expressed, thereby permitting cell growth, and wherein said second chromosomal gene is a host cell gene and is essential for cell growth.

4. The host cell of any of claims 1–3 wherein said repressor is a bacterial repressor.

5. The host cell of claim 1 wherein said bacterial repressor is selected from the group consisting of the *E. coli* lac repressor and the *E. coli* ArgRNV repressor.

6. The host cell of any of claims 1–3 wherein said cell is a bacterial cell.

7. The host cell of claim 6 wherein said cell is a gram negative bacterial cell.

8. The host cell of claim 7, said cell being *E. coli*.

9. The host cell of any of claims 1–3 wherein said plasmid comprises an origin of replication permitting replication of about 10–200 copies of said plasmid per host cell.

10. The host cell of claim 9 wherein said plasmid comprises an origin of replication permitting replication of about 100–200 copies of said plasmid per host cell.

11. The host cell of claim 10, said plasmid comprising a pUC origin of replication.

12. The host cell of any of claims 1–3 wherein said plasmid comprises a cloning site for insertion of a gene of interest.

13. The host cell of any of claims 1–3, said plasmid further comprising a gene of interest operatively associated with control sequences for expression of said gene in a mammalian cell.

14. The host cell of any of claims 1–3 wherein said plasmid consists essentially of an operator that binds to a repressor, an origin of replication, and a cloning site for insertion of a gene of interest.

15. The host cell of claim 14 wherein said plasmid is about 1000 bp in length.

16. A method of maintaining a plasmid in a host cell in vitro comprising the step of culturing the transformed cell of any of claims 1–3 for a time and under conditions sufficient to permit said cell to grow.

17. A method of producing plasmid DNA in vitro, comprising the steps of
    culturing the transformed cell of any of claims 1–3 for a time and under conditions sufficient to permit said cell to grow, and
    isolating plasmid DNA from said cultured cell.

18. A method of producing a recombiniiant protein in vitro, comprising the steps of
    culturing the transformed cell of any of claims 1–3 for a time and under conditions sufficient to permit said cell to grow, and
    isolating plasmid DNA from said cultured cell.

* * * * *

SEQUENCE LISTING

<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: PCR primer

<400> SEQUENCE: 1
gtgcccgaat tccaattggc g                                      21

<210> SEQ ID NO 2
<211> LENGTH: 24
<212> TYPE: DNA
<213> ORGANISM: Artificial Sequence
<220> FEATURE:
<223> OTHER INFORMATION: PCR primer

<400> SEQUENCE: 2
cggcgtgaat tcatcgctca tccc                                   24

<210> SEQ ID NO 3
<211> LENGTH: 24
<212> TYPE: DNA
<213> ORGANISM: Artificial Sequence
<220> FEATURE:
<223> OTHER INFORMATION: PCR primer

<400> SEQUENCE: 3
caatgcagaa ttcacagaac atta                                   24

<210> SEQ ID NO 4
<211> LENGTH: 24
<212> TYPE: DNA
<213> ORGANISM: Artificial Sequence
<220> FEATURE:
<223> OTHER INFORMATION: PCR primer

<400> SEQUENCE: 4
cggcgtgaat tcatcgctca tccc                                   24

<210> SEQ ID NO 5
<211> LENGTH: 25
<212> TYPE: DNA
<213> ORGANISM: Artificial Sequence
<220> FEATURE:
<223> OTHER INFORMATION: PCR primer

<400> SEQUENCE: 5
tcatcggaat tccctggagt atcgg                                  25

<210> SEQ ID NO 6
<211> LENGTH: 25
<212> TYPE: DNA
<213> ORGANISM: Artificial Sequence
<220> FEATURE:
<223> OTHER INFORMATION: PCR primer

<400> SEQUENCE: 6
tgagctgaat tccatcgccg cgctg                                  25